(12) United States Patent
Haddadi

(10) Patent No.: US 8,794,762 B2
(45) Date of Patent: Aug. 5, 2014

(54) DEVICE AND A METHOD FOR MEASURING A CHARACTERISTIC READING DISTANCE OF AN INDIVIDUAL IN A NEAR VISION NATURAL POSTURE

(75) Inventor: Ahmed Haddadi, Charenton-le-Pont (FR)

(73) Assignee: Essilor International (Compagnie Generale d'Optique), Charenton le Pont (FR)

( * ) Notice: Subject to any disclaimer, the term of this patent is extended or adjusted under 35 U.S.C. 154(b) by 264 days.

(21) Appl. No.: 13/113,114

(22) Filed: May 23, 2011

(65) Prior Publication Data

US 2011/0292345 A1 Dec. 1, 2011

(30) Foreign Application Priority Data

May 25, 2010 (FR) ...................................... 10 02199

(51) Int. Cl.
*A61B 3/02* (2006.01)
(52) U.S. Cl.
USPC ............ 351/208; 351/222; 351/244; 351/246
(58) Field of Classification Search
USPC .................................. 351/208, 239, 244–246
See application file for complete search history.

(56) References Cited

U.S. PATENT DOCUMENTS

| 8,085,902 B2* | 12/2011 | Bonfiglio et al. ............. 378/115 |
| 2010/0066975 A1* | 3/2010 | Rehnstrom ................... 351/210 |
| 2010/0195051 A1* | 8/2010 | Murray et al. ................ 351/209 |

FOREIGN PATENT DOCUMENTS

| GB | 2 154 332 A | 9/1985 |
| JP | 2000-325309 A | 11/2000 |
| JP | 2005-144084 A | 6/2005 |
| JP | 2007-097707 A | 4/2007 |
| JP | 2009-160197 A | 7/2009 |

OTHER PUBLICATIONS

French Search Report, dated Jan. 14, 2011, from corresponding French application.

* cited by examiner

*Primary Examiner* — Jordan Schwartz
(74) *Attorney, Agent, or Firm* — Young & Thompson

(57) ABSTRACT

A measurement device for measuring a characteristic reading distance of an individual in a natural posture for near vision, includes a movable reading medium presenting a plane display portion suitable for displaying signs and a measurement subassembly including at least one ultrasound emitter member and at least one ultrasound receiver member. The emitter and receiver members are carried by the reading medium, and at least one of the members, referred to as the first measurement member possesses a measurement axis along which emission or reception by the first measurement member is privileged and that is inclined relative to the plane of the display portion by an angle lying in the range 10 degrees to 80 degrees or that is inclinable relative to this plane of the display portion at least over an angular range extending from 10 degrees to 80 degrees.

27 Claims, 4 Drawing Sheets

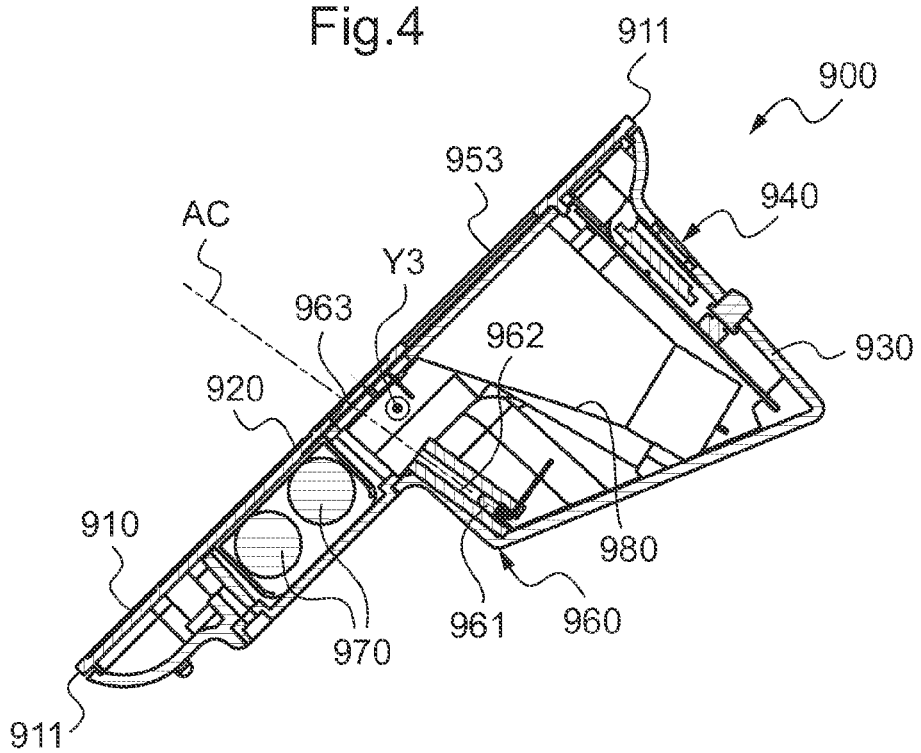
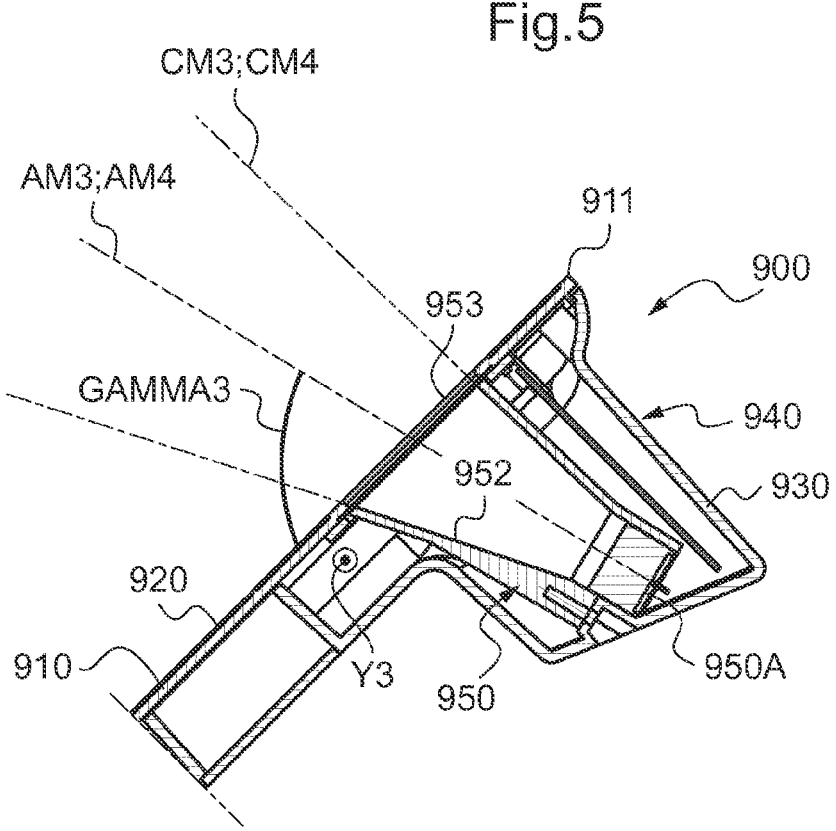

DEVICE AND A METHOD FOR MEASURING A CHARACTERISTIC READING DISTANCE OF AN INDIVIDUAL IN A NEAR VISION NATURAL POSTURE

TECHNICAL FIELD TO WHICH THE INVENTION RELATES

The present invention relates to a device for measuring a characteristic reading distance of an individual in a natural posture and in near vision.

The invention also relates to a method of measuring such a distance by means of such a device.

TECHNOLOGICAL BACKGROUND

Determining the natural distance taken up by an individual relative to a text for the purpose of reading it is very important when preparing ophthalmic lenses that provide their wearer with personalized optical correction and that are particularly adapted to the individual's near vision.

Document JP 2007-097707 discloses a device enabling said distance to be determined, the device comprising firstly a reading medium made in the form of a tablet placed at a distance that is appropriate for reading a text carried by said tablet, and secondly means for measuring the distance of the head relative to the tablet. Those distance-measuring means typically make use of ultrasound.

In that device, the ultrasound emitter or receiver is placed on the individual's eyeglass frame. That presents the drawback of making it impossible to perform the measurement under conditions in which the individual is in a natural posture, i.e. conditions in which the individual is free to take up any desired position relative to the tablet, so as to occupy reading conditions that are the most comfortable for the individual. It will readily be understood that the presence of an ultrasound emitter or receiver on the individual's eyeglass frame necessarily puts a constraint on the individual's posture.

Another solution as disclosed in document JP 2000-325309 consists in placing the ultrasound emitter and receiver on the tablet and in detecting the ultrasound as emitted and reflected on the individual's head. That method presents the drawback of being relatively inaccurate.

In that known device, the measurement axis of the emitter and of the receiver is substantially perpendicular to the plane of the reading portion of the tablet. In order to enable a measurement to be taken, it is therefore necessary to place the tablet in such a manner that the measurement axes of the emitter and of the receiver point towards the individual, and thus that the plane of the reading portion of the tablet is oriented facing the individual. Unfortunately, that configuration does not correspond to a natural reading posture.

OBJECT OF THE INVENTION

An object of the present invention is to propose a device and a method for measuring a near vision reading distance of an individual in that individual's natural posture, which method and device are fast, accurate, and easy to use, with as little constraint as possible on the individual's posture.

To this end, the invention provides a measurement device for measuring a characteristic reading distance of an individual in a natural posture for near vision, the device comprising:

a portable or freely movable reading medium presenting a plane display portion suitable for displaying signs; and a measurement subassembly including at least one ultrasound emitter member and at least one ultrasound receiver member;

wherein the emitter and receiver members are carried by the reading medium, and wherein at least one of said members, referred to as the first measurement member, possesses a measurement axis along which emission or reception by the first measurement member is privileged and that is inclined relative to the plane of the display portion by a constant angle lying in the range 10 degrees to 80 degrees or that is inclinable relative to this plane of the display portion at least over an angular range extending from 10 degrees to 80 degrees.

The device of the invention thus makes it possible to allow the individual whose characteristic reading distance is to be measured to place the display portion of the reading medium on which the individual is going to read signs at a distance that can be freely chosen relative to the individual's eyes, and in particular relative to the ophthalmic lenses of an eyeglass frame, so as to take a measurement under natural posture conditions of the individual.

In a natural posture, the plane of the display portion is inclined in front of the individual's face.

The measurement is performed using a conventional principle of measuring distance by ultrasound: the receiver member detects ultrasound signals that have been emitted by the emitter and reflected on the individual's head, or more precisely on an accessory placed on the individual's head. In practice, it is particularly advantageous to perform this measurement by ultrasound since the difference in reflectivity between the individual's skin and the accessory, typically the frame and the ophthalmic lenses of a pair of eyeglasses worn on the individual's head, makes it possible to determine easily which signal is reflected by the accessory.

The measured characteristic reading distance is thus preferably the distance between the individual's eyeglass frame and the measurement device.

In order to take the measurement easily, it is advantageous to use an ultrasound emitter member that emits in a measurement cone presenting an angle at the apex that is wide enough to make it easy to cover all of the individual's head, or at least the accessory worn by the individual's head. The angle at the apex of the measurement cone of the emitter member should thus be greater than or equal to 15 degrees.

In order to take a measurement that is accurate, it is advantageous to use a first measurement member that emits or receives ultrasound exclusively in a measurement cone having an angle at the apex that is less than or equal to 45 degrees.

It is then useful to verify that the individual's head does indeed lie in this measurement cone.

More particularly, in order to optimize the ultrasound signal measured by the measurement device, it is then preferable to orient the measurement axis of the first measurement member substantially perpendicularly to the mean plane of the individual's eyeglass frame.

Such an orientation for the measurement axis of the first measurement member serves advantageously to provide a measurement that is accurate, in particular by measuring a signal that presents a satisfactory signal-to-noise ratio.

The measurement member includes at least one emitter, receiver, or emitter-receiver measurement element placed in a body. The term "measurement axis" is used herein to mean an axis along which emission or reception by the first measurement member is privileged. For a receiver member, the measurement axis corresponds to the axis passing through the receiver element and on which the intensity of the received ultrasound signal is at its maximum when the axis is pointing at an ultrasound source. For an emitter member, the measurement axis corresponds to the axis passing through the emitter element and on which the intensity of the emitted ultrasound signal is at a maximum when the axis is pointing at an ultrasound receiver element.

For an emitter-receiver member, the measurement axis corresponds to the axis on which a maximum intensity signal is detected for an emitted signal of determined intensity.

In practice, the measurement axis corresponds to an axis of symmetry of the body of the measurement member. By way of example, the body is typically in the form of a cylindrical or conical cavity with the measurement element placed at the end thereof. The measurement axis then corresponds to the longitudinal axis of the cylindrical cavity or to the axis of revolution of the conical cavity.

The measurement cone of the measurement member then designates a solid angle representing all of the ultrasound propagation axes in three dimensions along which ultrasound waves are emitted or received by the measurement member. The solid angle is centered on the measurement axis and corresponds substantially to the solid angle defined by the conical cavity.

With the measurement axis inclined relative to the plane of the display portion at an angle lying in the range 10 degrees to 80 degrees, or inclinable at least over an angle lying in the range 10 degrees to 80 degrees, the modification in inclination needed to bring the measurement axis into the direction perpendicular to the plane of the ophthalmic lenses of the individual's eyeglass frame is limited. This therefore gives rise to a limited modification to the angle of inclination of the display portion, or indeed to no modification of said angle of inclination of the display portion.

In a simplified embodiment of the invention, the first measurement member is mounted stationary on the reading medium. The measurement axis is then inclined at a non-varying angle lying in the range 10 degrees to 80 degrees relative to the plane of the display portion.

The modification needed to the angle of inclination of the display portion in order to orient the measurement axis of the first measurement member perpendicularly to the plane of the ophthalmic lenses of the wearer's pair of eyeglasses is then limited relative to the modification that would be necessary if the measurement axis were, in conventional manner, at an angle of 90 degrees relative to the plane of the display portion.

The display portion then remains close to the angle of inclination in which the individual placed it initially, thus corresponding to an angle of inclination in a natural posture. The reading distance selected by the individual remains natural for measuring the characteristic reading distance.

In an improved embodiment of the invention, the first measurement member is movably mounted on the reading medium to be capable at least of pivoting relative to the plane of said display portion of the reading medium.

Pivoting the first measurement member relative to said display portion then enables the orientation of the measurement axis of the first measurement member to be varied independently of the position and the orientation in three dimensions of the display portion of the reading medium. The display portion can thus remain in the position selected by the individual and corresponding to the individual's natural reading posture, while the angular position of the measurement axis of the first measurement angle is adjusted so that the individual's head comes within the measurement cone of said member, and preferably so that its measurement axis is perpendicular to the mean plane of the individual's eyeglass frame.

The mean plane of the eyeglass frame corresponds to a first approximation to the mean plane of the ophthalmic lenses mounted in the frame.

The angle of inclination of the device and the reading distance selected by the individual then remain entirely natural while the characteristic reading distance is being measured.

This ability of the first measurement member to pivot enables the detected ultrasound signal to be finely optimized and consequently serves to improve the accuracy of the distance measurement taken.

According to other characteristics of the device of the invention that are advantageous and non-limiting:
   at least one emitter member and at least one receiver member are mounted to pivot together on the reading medium;
   said measurement subassembly includes a measurement support that is mounted to pivot on the reading medium and that carries the emitter and receiver members;
   said first measurement member presents a measurement cone centered on its measurement axis, the angle at the apex of the cone being less than 45 degrees;
   the device includes visual detection means enabling the individual to detect visually a relative position of said first measurement member and the head of the individual in which the individual's head is situated at least in part in the measurement cone of said first measurement member, in a determined relative position of the head and the reading medium;
   the device includes automatic detection means for automatically detecting a relative position of said first measurement member and the head of the individual in which the individual's head is situated at least in part in the measurement cone of said first measurement member, in a determined relative position of the head and the reading medium;
   said first measurement member is a receiver member;
   said first measurement member is an emitter member;
   said visual detection means comprise at least one target secured to said measurement member; and
   said automatic detection means include means for scanning a range of angular positions of said first measurement member relative to the display portion of the reading medium, so that the measurement axis of the first measurement member scans the individual's head.

The invention also provides a method of measuring a characteristic reading distance of an individual in a natural posture and in near vision.

In a simplified implementation of the invention, the method comprises the following steps:
   a1) providing the individual with a measurement device comprising:
      a portable or freely movable reading medium presenting a plane display portion suitable for displaying signs; and
      a measurement subassembly including at least one ultrasound emitter member and at least one ultrasound receiver member carried by the reading medium, at least one of said members, referred to as a first measurement member mounted in stationary manner on the reading medium and possessing a measurement axis along which emission or reception by the first measurement member is privileged and that is inclined relative to the plane of the display portion by a constant angle lying in the range 10 degrees to 80 degrees;
   b1) the individual positioning the display portion of the reading medium in an appropriate reading position enabling the individual to read the signs on the display portion; and d1) in the configuration defined in step b1), determining the looked-for characteristic distance as a function of the signal delivered by the receiver member and representative of the ultrasound signal emitted by the emitter member and reflected.

This method presents the advantage of being quick and easy to use and of providing an accurate measurement of the looked-for characteristic reading distance.

According to other characteristics of the method in this simplified embodiment and that are advantageous and non-limiting:

the method further includes the following step c1): in a reading position set in step b1), causing the reading medium as a whole to pivot so as to place said first measurement member in an angular position in which the receiver member picks up, with maximum intensity or intensity greater than the threshold, the ultrasound emitted by the emitter member and reflected by the head of the individual or by an accessory worn on the head; and in step d1), the looked-for characteristic distance is determined in the configuration defined in steps b1) and c1);

in step c1), for said first measurement member presenting a measurement cone having an angle at the apex of less than 45 degrees, the reading medium is caused to pivot to place said first measurement member in an angular position such that the individual's head is situated at least in part in the measurement cone of the first measurement member;

in step c1), for the device including at least one target and at least one mark secured to said first measurement member, the mark and the target being offset from each other along the direction of the measurement axis of the measurement member, the individual causes the reading medium to pivot in such a manner as to center said target on said mark visually;

for the device including at least one target secured to said first measurement member and located at the end of a cavity in such a manner that the target is visible to the individual only in a predetermined range of orientation angles of the measurement member relative to the individual's head, in step c1), the individual causes the reading medium to pivot in such a manner as to be able to see the target; and in step c1), the reading medium is caused to pivot about a horizontal axis situated in the mean plane of the reading medium.

In an improved implementation of the method of the invention, the method comprises the following steps:

a2) providing the individual with a measurement device comprising:

a portable or freely movable reading medium presenting a plane display portion suitable for displaying signs; and a measurement subassembly including at least one ultrasound emitter member and at least one ultrasound receiver member carried by the reading medium, at least one of these members, referred to as the first measurement member being mounted on the reading medium to be capable at least of pivoting relative to said display portion of the reading medium and possessing a measurement axis along which the emission or the reception by the first measurement member, is privileged;

b2) the individual positioning the display portion of the reading medium in a suitable reading position enabling the individual to read the signs of the display portion;

c2) in this reading position set in step b2), causing said first measurement member to pivot relative to the display portion to place said first measurement member in an angular position in which the receiver member picks up, with maximum intensity or intensity greater than a threshold, the ultrasound emitted by the emitter member and reflected by the individual's head or by an accessory worn by the head; and d2) in the configuration defined in steps b2) and c2), determining the looked-for characteristic distance as a function of the signal delivered by the receiver member and representative of the ultrasound signal emitted by the emitter member and reflected.

In this improved implementation, the angle of inclination of the measurement axis of the first measurement member is set more finely and the display portion may be positioned in completely free manner.

The measurement taken in this improved implementation of the method thus corresponds to the individual being in a posture that is as close as possible to a natural posture.

According to other characteristics of this improved implementation of the method of the invention:

in step c2), for said first measurement member presenting a measurement cone having an angle at the apex of less than 45 degrees, said first measurement member is caused to pivot relative to the display portion to place it in an angular position in which the individual's head is situated at least in part in the measurement cone of the first measurement member;

in step c2), for the device including at least one target and at least one mark secured to said first measurement member, the mark and the target being offset along the direction of the measurement axis of the first measurement member, the individual causes the first measurement member to pivot in such a manner as to center said target on said mark visually;

for the device including at least one target secured to said first measurement member and located at the end of a cavity in such a manner that the target is visible to the individual only over a predetermined range of orientation angles of the measurement member relative to the individual's head, in step c2) the individual causes the first measurement member to pivot in such a manner as to be able to see the target;

in step c2), the following steps are performed:
causing the ultrasound emitter member to emit ultrasound;
manually or automatically scanning the various possible angular positions of the first measurement member during ultrasound emission;
detecting an ultrasound signal as emitted and reflected by the individual's head or by an accessory worn by the head during said scanning; and
as a function of the detected signal, determining the looked-for angular position of the first measurement member in which the receiver member picks up the ultrasound emitted by the emitter member and reflected; and in step c2), the first measurement member is caused to pivot relative to the display portion of the reading medium about a horizontal axis situated in the mean plane of the reading medium.

BRIEF DESCRIPTION OF THE DRAWINGS

The following description with reference to the accompanying drawings given by way of non-limiting example makes it understood what the invention consists in and how it can be reduced to practice.

In the accompanying drawings:

FIGS. 4 and 5 are diagrammatic section views of the FIG. 3 measurement device on planes P1 and P2, respectively;

DETAILED DESCRIPTION OF THE PREFERRED EMBODIMENTS

In the description below, the optician determines a reading distance that is characteristic of an individual.

As shown in FIGS. 2, 6, 7, and 9, the head 10 of an individual is fitted with an accessory 30 that is preferably constituted by an eyeglass frame 30 (see FIG. 6) fitted with eyesight-correcting ophthalmic lenses 31D, 31G.

The individual may be sitting or standing.

The vertical direction is defined herein as the direction given by a plumb line at a given location. A horizontal direction is perpendicular to the vertical direction.

Figure 6:
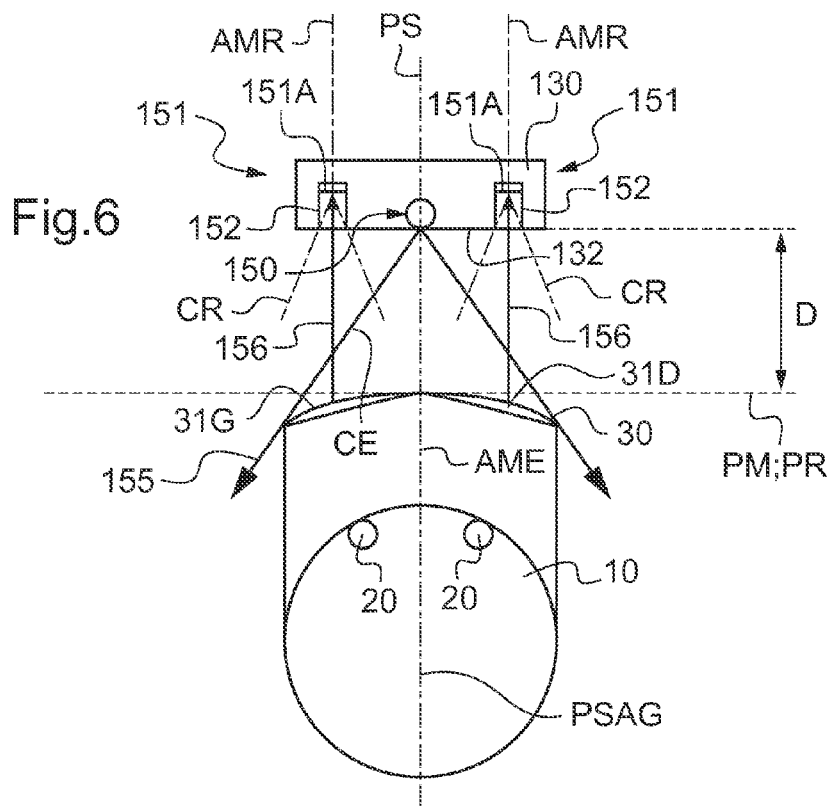
FIG. 6 is a diagrammatic plan view of an individual's head and of the measurement subassembly of the FIG. 1 device placed facing the individual's face.

A sagittal plane PSAG of the individual's head is a midplane of the individual's head passing halfway between the two centers of rotation of the eyes 20 and perpendicular to the straight line interconnecting the two centers of rotation of the eyes 20 (FIG. 6). The sagittal plane is substantially vertical when the individual is sitting or standing in a natural posture.

Figure 9:
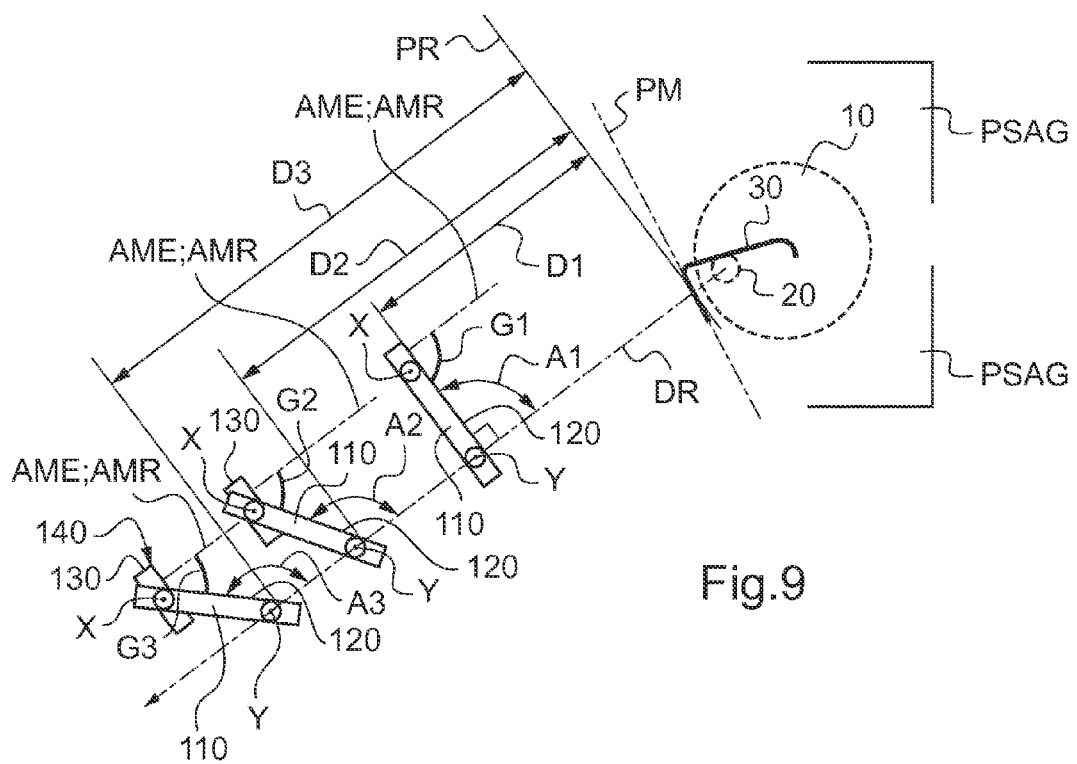
FIG. 9 is a diagrammatic profile view of the individual's head relative to the measurement subassembly of the FIG. 1 device.
Figure 7:
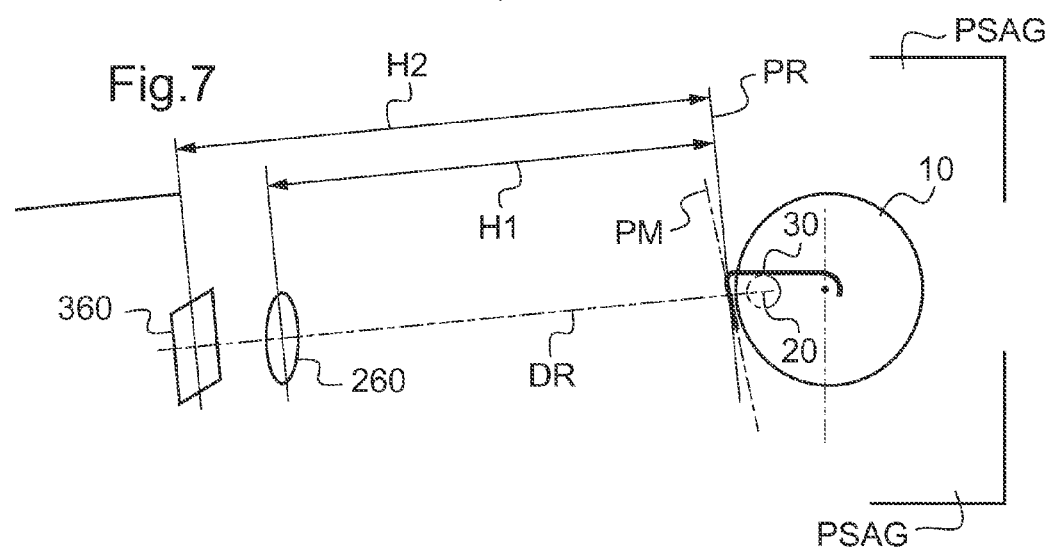
FIG. 7 is a diagrammatic profile view of the head of the individual and of a portion of the measurement device, showing the principle of visual centering by parallax of a target and a mark associated with a measurement member of the measurement subassembly for adjusting the orientation of the measurement axis of the first measurement member relative to the individual's head in order to place said measurement axis in an angular position for which the receiver member picks up the ultrasound emitted by the emitter member and reflected by the individual's head or by an accessory placed thereon.

A gaze direction DR is defined as the straight line bisecting the angle between the lines connecting each of the individual's eyes to the point at which the individual is gazing (FIGS. 7 and 9).

A gaze plane PR is also defined as being perpendicular to the gaze direction DR (FIGS. 6, 7, and 9). To a first approximation, the gaze plane PR coincides with the mean plane PM of the frame 30, as shown in FIG. 6.

The mean plane PM of the frame 30 in this example coincides with the mean planes of the corresponding ophthalmic lenses.

FIGS. 1, 2, and 3 to 5 show respectively an improved embodiment and two simplified embodiments of the measurement device of the invention, referenced 100, 800, and 900. The device shown in FIGS. 3 to 5 constitutes a preferred embodiment.

The measurement device 100, 800, 900 includes a reading medium in the form of a freely movable or portable tablet 110, 810, 910.

The tablet 110, 810, 910 is generally rectangular in shape, being defined by transverse edges 111, 811, 911 and longitudinal edges 112, 812, 912 that are parallel and opposite. In a variant, it is possible to provide for it to be of arbitrary shape.

The tablet 110, 810, 910 includes on its front face, i.e. on its side that is to face towards the individual's head 10, a plane display portion 120, 820, 920 having signs 121, 821, 921 displayed thereon, on which signs the individual gazes while a measurement is being taken.

The signs 121, 821, 921 are typically aligned in a plurality of display lines, each comprising for example optotypes similar to those used by an optician to evaluate an individual's vision defects. It may also be constituted by an arbitrary text that the individual reads.

This display portion 120, 820, 920 may include signs that are stationary or a display screen that is dynamic enabling different signs to be displayed, for example enabling texts to be displayed in which the letters used present different heights.

The tablet 110, 810, 910 is preferably portable and the individual holds it in both hands while a measurement is being taken.

Nevertheless, it may be useful to prevent the tablet from being removable, e.g. in order to avoid the tablet being stolen from an optician's office.

Under such circumstances, the tablet may be mounted for example on an arm that allows the position of the tablet to be adjusted in three dimensions in front of the individual, in particular concerning the distance between the tablet and the individual's head in a horizontal plane, and the height between the tablet and the individual's head in a vertical plane, and also the angle of inclination of the tablet about a horizontal axis.

The individual can then adjust the position of the tablet by hand by varying those parameters or by causing them to vary under remote control, or indeed by giving instructions to an operator for causing the tablet to be placed in a position where the individual finds reading comfortable.

In a variant, the tablet may also be placed on a table, the table being adapted to be moved so that the individual takes up a natural reading posture relative to the table.

In any event, the individual adjusts the relative position between the tablet and the individual's own head so as to find a reading position that is natural and comfortable. The tablet 110, 810, 910 is then in a reading position that is suitable for the individual.

It is assumed that in this reading position that is natural and comfortable for the individual, the individual maintains the sagittal plane PSAG of his or her head vertical.

It is also assumed that in order to read the text or to view the signs on the display portion 120, 820, 920, the individual preferably places said display portion 120, 820, 920 substantially directly in front of him.

The display portion 120, 820, 920 is preferably situated in a middle zone of the tablet 110, 810, 910 so that the tablet 110, 810, 910 extends on either side of the sagittal plane PSAG of the individual's head.

Finally, in a reading position that is natural and comfortable for the individual, the individual preferably orients the text or the signs for reading horizontally. This requires the tablet 110, 810, 910 to be pivoted about a horizontal axis Y1, Y2, Y3 (FIGS. 1, 2, 4, and 5) that is parallel to the text in the display portion 120, 820, 920. Furthermore, the individual holds the display portion of the text for reading in a plane that is substantially perpendicular to the sagittal plane of the individual's (FIG. 6).

Alternatively, provision may be made for the individual also to adjust the orientation of the tablet about an axis perpendicular to said horizontal axis and parallel to the plane of the display portion. This corresponds to the measurement device performing a tilting movement from left to right or from right to left.

When the tablet 110, 810, 910 is generally rectangular, as in the embodiments of FIGS. 1, 2, and 3 to 5, the signs 121, 821, 921 or the text for reading in the display portion are thus preferably oriented parallel to two opposite edges of the tablet 110, 810, 910, the transverse edges 111, 811, 911, in this example.

This makes it easier for the individual to handle the tablet 110, 810, 910.

The measurement device 100, 800, 900 also includes a measurement subassembly 140, 840, 940 including various measurement members, including at least one ultrasound emitter member and at least one ultrasound receiver member.

As explained in greater detail below, the measurement device may include either at least one ultrasound emitter member and at least one ultrasound receiver member that are separate and distinct, or else a single member that is both an emitter and a receiver of ultrasound.

The measurement subassembly 140, 840, 940 and the display portion 120, 820, 920 of the tablet 100, 800, 900 preferably presents a common plane of symmetry PS.

The plane of symmetry PS substantially coincides with the sagittal plane PSAG of the individual's head 10 in the reading position.

Figure 1:
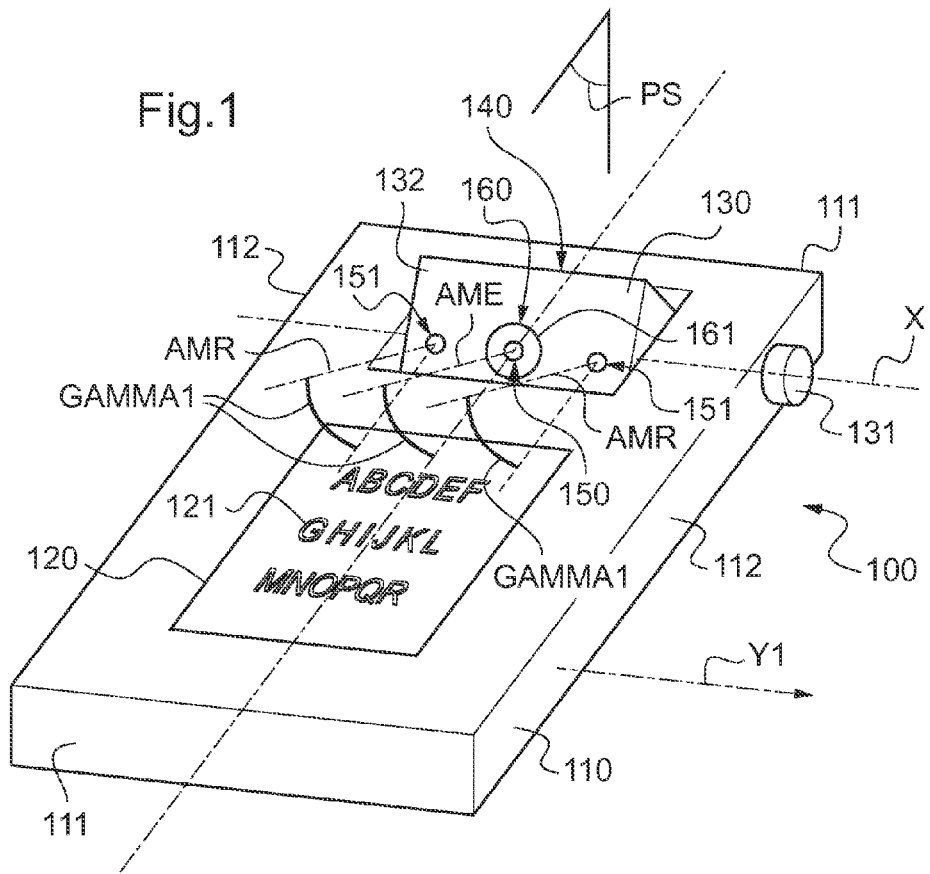
FIG. 1 is a perspective view of an embodiment of the measurement device in the improved embodiment of the invention.

In the improved embodiment of the invention shown in FIG. 1, said measurement subassembly 140 comprises, for example, a single emitter member 150 and two receiver members 151.

All three of these measurement members 150, 151 are carried by the tablet 110. They are in alignment on a line that is parallel to the display lines of the signs 121 on the display portion 120, and thus parallel to the transverse edges 111 of the tablet 110.

More precisely, the emitter member 150 is located halfway between the receiver members 151. These two receiver members 151 are 7 centimeters apart in this example. This spacing enables each receiver member to be placed facing one of the ophthalmic lenses 31D, 31G of the frame 30.

In remarkable manner, the emitter and receiver members 150 and 151 are carried by the tablet 110 and at least one of these emitter and receiver members 150 and 151 possesses a measurement axis AMR, AME on which emission or reception is favored, which axis can be tilted relative to the plane of the display portion 120 over at least an angular range of 10 degrees to 80 degrees.

The emitter or receiver member 150 or 151 in question is more precisely movably mounted on the tablet 110 so as to be capable at least of pivoting relative to the display portion 120 thereof.

More particularly, in the example shown in the figures, all three emitter and receiver members 150 and 151 are movably mounted on the tablet 110.

All three of them are mounted to pivot together on the tablet 110. The measurement axes AME, AMR1, and AMR2 of these emitter and receiver members 150 and 151 are then all inclined at the same angle GAMMA1 relative to the plane of the display portion 120.

In a particularly advantageous variant of this improved embodiment, the measurement subassembly has two members that are both emitters and receivers of ultrasound, and at least one of those emitter-receiver members possesses a measurement axis on which emission or reception is favored and that is tiltable relative to the plane of the display portion over at least an angular range of 10 degrees to 80 degrees.

These two emitter-receiver members are preferably spaced apart by 7 centimeters so that each of them is placed facing a respective one of the ophthalmic lenses of the frame.

In another variant, the measurement subassembly has only one emitter-receiver member that is located centrally. The operation of the measurement device remains the same.

The measurement subassembly 140 in this example includes a measurement support 130 that is pivotally mounted on the tablet 110 and that carries the emitter and receiver members 150 and 151.

The measurement support 130 is pivotally mounted about a pivot axis X that is parallel to the line on which the emitter 150 and the receivers 151 are in alignment, and thus perpendicular to the plane of symmetry PS of the measurement subassembly 140 and of the display portion 120.

By way of example, the measurement support 130 is adapted to be tilted at least over a range of angles of inclination such that the angle GAMMA1 lies in the range 10 degrees to 80 degrees.

Preferably, the measurement support 130 pivots through an angle of at least 15 degrees towards the front or the rear of the tablet 110 relative to a reference middle angular position in which the angle GAMMA1 lies in the range 10 degrees to 80 degrees.

When the tablet 110 is placed by the individual in the reading position, this pivot axis X is maintained substantially horizontal.

In this example, the pivoting of the measurement support 130 about the pivot axis X is controlled manually by the individual using a knob 131.

In a variant, the measurement support may be mounted on the tablet via a hinge, and the individual may pivot the support manually by acting on it directly. No knob is then provided.

Thus, as shown in FIG. 9, whatever the angle of inclination A1, A2, A3 of the display portion 120 relative to the gaze line DR in the sagittal plane PSAG of the individual's head in the reading position, it is possible to cause the measurement subassembly 140 to pivot about the pivot axis X in order to point the emitter and receiver members 150 and 151 towards the individual's head.

It is then possible to position the emitter and receiver members 150 and 151 of the subassembly 140 accurately relative to the individual's head so as to optimize the detected ultrasound signal, i.e. so as to obtain an ultrasound signal of maximum intensity or of intensity greater than a threshold.

To do this, and as shown in FIG. 9 and described in detail below, the measurement axes AME and AMR are of the emitter and receiver members 150 and 151 of the measurement subassembly 140 are inclined at respective angles G1, G2, and G3 relative to the display portion 120 when it is inclined at an angle equal to A1, A2, and A3, such that the measurement axes AME and AMR of the emitter and receiver members 150 and 151 remain perpendicular to the frame plane PM coinciding with the gaze plane PR, regardless of the angle of inclination of the display portion 120 (FIG. 9).

Using a conventional principle for measuring distance by means of ultrasound, the receiver members 151 detect ultrasound signals emitted by the emitter 150 and reflected on the wearer's head 10 (see FIG. 6).

The measurement device 100 includes electronic and computer means (not shown) for processing the ultrasound signal detected by the receiver members.

Ultrasound is reflected more effectively when the surface on which it is reflected is hard. The ultrasound signal reflected on the eyeglass frame 30 and the ophthalmic lenses 31D, 31G mounted on said frame 30 is thus much stronger than the ultrasound signal corresponding to ultrasound reflected on the individual's skin. The position of the frame 30 of the individual wearing the ophthalmic lenses can thus be detected easily and accurately since the detected ultrasound signal is stronger and less subjected to variations due to interfering signals.

The measured reading distance characteristic of the individual in this example is thus preferably the distance between the emitter member 150 of the tablet 110 and the individual's eyeglasses 30.

This distance is referenced D in FIG. 6.

FIG. 9 shows three possible reading positions for the tablet 110. The first position corresponds to a reading distance D1 and an angle of inclination A1 of the tablet 110 relative to the gaze direction DR. The second position corresponds to a reading distance D2 and to an angle of inclination A2 of the tablet 110 relative to the reading direction DR. The third position corresponds to a reading distance D3 and to an angle of inclination A3 of the tablet 110 relative to the gaze direction DR.

By way of example, the distance D1 is equal to 25 centimeters (cm) and the angle A1 is equal to 90 degrees. The distance D2 is equal to 40 cm and the angle A2 is equal to 110 degrees. The distance D3 is equal to 50 cm and the angle A3 is equal to 130 degrees.

In the improved embodiment shown in FIGS. 1, 6, and 9, it is preferable to use an emitter member 150 that emits ultrasound over a wide solid angle, e.g. presenting an angle at the apex that is greater than or equal to 45 degrees. This solid angle corresponds to the measurement cone CE of the emitter member, which is in this example an emission cone CE (FIG. 6). This emission cone CE is defined in FIG. 6 by arrows 155 representing emitted ultrasound waves. It is centered about the measurement axis AME that constitutes a privileged ultrasound emission direction of the emitter member.

There is no need for the positioning of the emitter member 150 relative to the individual's head 10 to be adjusted very accurately, since the emission cone CE of the emitter 150 covers a wide measurement cone and approximate positioning of the tablet 110 in front of the individual's eyes 20 ensures that the individual's head 10 enters into the emission cone at least in part and thus receives ultrasound waves that it reflects.

In contrast, the receiver members 151 that are used presents respective measurement cones CR (FIG. 6) centered on their measurement axes AMR that constitute the privileged ultrasound reception directions of each of the receiver members 151. As shown, the reception cones CR present an angle at the apex of less than 45 degrees.

In this example, each receiver member 151 has a receiver element 151A placed in a body that presents the form of a cylindrical orifice 152 set back in the front face of the measurement device 100. More precisely, the cylindrical orifices 152 are set back in the front face of the measurement support 130, as shown in FIG. 6.

The receiver members 151 thus receive only ultrasound waves reflected by the individual's head 10 and more particularly by the frame 30 placed on the individual's head in a direction that is very close to the longitudinal axis of the cylindrical orifice 152 (FIG. 6), representing the respective measurement axes AMR of the receiver members 151, perpendicular to the front face 132 of the measurement support 130. This applies for example to the ultrasound waves represented by arrows 156 in FIG. 6.

The reception cone CR of the receiver member 151 is limited by the outline of the cylindrical orifice 152, regardless of the intrinsic reception cone of the receiver element that is used.

In the example shown in FIGS. 1, 6, and 9, the measurement axes AMR and AME of the receiver and emitter members 151 and 150 of the measurement device 100 are mutually parallel and perpendicular to the front face 132 of the measurement support 130.

These receiver and emitter members are mounted on the tablet 110 to pivot together relative to the display portion 120, and they thus all form the same angle GAMMA1 with the plane of the display portion 120, which angle may be modified by pivoting the measurement support 130 at least over the above-mentioned range of angles of inclination of the measurement device 100.

In a variant, it is possible to envisage that these measurement axes are not mutually parallel. Their angles of inclination may serve to take account of the eyeglass frame worn by the individual presenting strong curvature.

The ultrasound waves reflected along the measurement axis AMR of each receiver member 151 come from a surface that is substantially perpendicular to the longitudinal axis of the cylindrical orifice 152. That is why it is particularly important in this example to incline the receiver members 151 in such a manner that the longitudinal axes of the cylindrical orifices 152 coinciding with the measurement axes AMR of the corresponding receiver members 151 are substantially perpendicular to the mean plane PM of the individual's eyeglass frame 30 (FIGS. 1, 6, and 9).

This corresponds to an angular position of the measurement support 130 in which the front face 132 of the measurement support 130 is substantially parallel to the mean plane PM of the frame 30.

As mentioned above, to a first approximation, the mean plane PM of the frame 30 coincides with the gaze plane PR perpendicular to the gaze direction DR. In practice, it differs therefrom by only a few degrees and this approximation leads to only a small amount of error in the distance measurement.

The measurement support 130 thus needs to be placed in an angular position such that it is perpendicular to the gaze direction DR.

Alternatively, provision may be made for the receiver members to present wide reception cones and for the emitter member to present a narrow emission cone.

In order to determine the angular position of the measurement support 130 about the pivot axis X, which position is suitable for detecting ultrasound reflected on the individual's eyeglass frame 30, the device includes visual detection means 160 enabling the individual to detect visually a relative position of the receiver members 151 and the individual's head 10 in which the mean plane PM of the frame is substantially perpendicular to the measurement axes AMR of the receiver members 151 in order to detect a signal of maximum intensity or at least greater than a threshold.

This adjustment then ensures that the head 10 is situated at least in part within the reception cones CR of the receiver members 151 (FIG. 6) for a predetermined read position of the tablet 110 relative to the individual's head.

As shown in FIG. 1, these visual detection means 160 comprise at least one target 161 secured to the receiver members 151. The target 161 in this example is constituted by a circle 161 located in the thickness of the measurement support 130, in a plane parallel to the front face 132 of the measurement support 130 facing towards the individual, and set back from said front face 132.

The target 161 faces the emitter member 150 carried by the front face 132 of the measurement support 130.

The measurement support 130 is preferably made of a transparent material, e.g. a transparent plastics material, at least for its thickness lying between said front face 132 and the target 161.

The target 161 is placed in such a manner that when the measurement support 130 is observed along the gaze direction DR perpendicular to its front face 132, the emitter 150, which then performs a marking function, appears to be situated at the center of the circle of the target 161.

When the measurement support 130 is observed in a gaze direction DR that is not perpendicular to its front face, the emitter 150 appears off-center relative to the circle of the target 161, since it is situated in a plane that is different from the plane of the emitter 150. This is due to a parallax phenomenon.

Once the individual has placed the display portion 120 of the tablet 110 in its read position, it is then possible for the individual to observe the relative position of the emitter 150 and the target-forming circle 161 in order to determine whether the front face 132 of the measurement support 130 is perpendicular to the gaze direction DR.

If not, the individual causes the angular position of the measurement support 130 to vary relative to the display portion 120 of the tablet about the pivot axis X by manually actuating the knob 131.

When the individual sees the emitter 150 centered in the target 161, the measurement support 130 should be stopped so as to remain in this angular position to enable a measurement to be taken. The longitudinal axis of the cylindrical orifice 152 is then substantially perpendicular to the mean plane PM of the frame, thus ensuring that the directional receiver members 151 are in a suitable position relative to the eyeglasses 30 of the individual in order to take the measurement.

Alternatively, if the receiver members are directional without being placed at the ends of cylindrical orifices, then it is the bisector of the reception cone of each receiver member that acts as the measurement axis AMR of the receiver member and that is oriented perpendicularly to the mean plane PM of the frame.

In a variant, the pivoting of the measurement support may be motor-driven and controlled by an electronic control unit. The individual then launches a scan of all possible angular positions of the measurement support, which scan is stopped when the target is centered around the emitter.

In another variant, the measurement support may be mounted on the tablet by means of a hinge, with scanning being performed either manually by the individual pivoting the support by acting directly thereon, or automatically if the pivoting of the support is motor-driven. No knob is then provided.

In a variant, the device may include marks that are distinct for the emitter and receiver members.

Figures 8A, 8B, 8C:
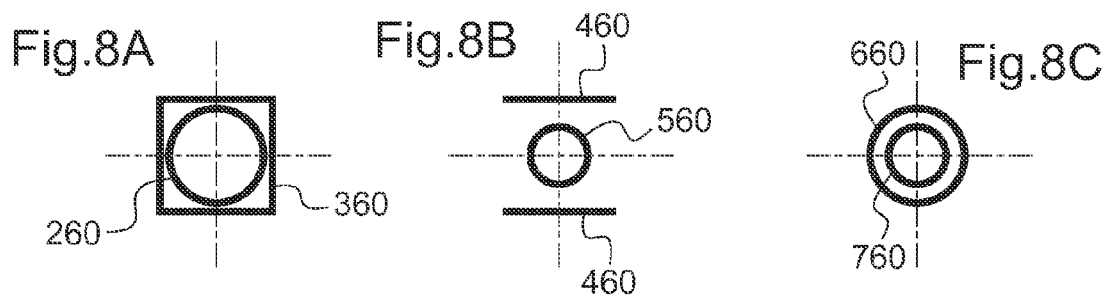
FIGS. 8A, 8B, and 8C are detail front views respectively showing three variant embodiments of the target and of the mark when they are centered, i.e. when the emitter and receiver members are pointing towards the individual's face.

The principle on which angular position is adjusted is then represented in FIG. 7 and FIGS. 8A, 8B, and 8C which show various shapes of targets and marks forming the visual detection means. The marks 260, 560, 760 are situated in a first plane, and the targets 360, 460, 660 are located in a second plane parallel to the first plane and distinct therefrom, the first and second planes being situated at different distances H1 and H2 from the individual's head in the gaze direction DR (FIG. 7). To the individual they appear centered relative to each other when the gaze direction is perpendicular to the planes containing them (FIGS. 8A, 8B, 8C).

FIGS. 8A, 8B, 8C show various pairs of targets and marks that are suitable for being used: a circle 260 in the center of a square 360; a circle 560 between two parallel lines 460; or two concentric circles 660 and 760.

In another variant, the target of the visual detection means may be placed at the bottom of a cavity formed in the front face of the measurement support so that it is visible to the individual only when the measurement support is in an angular position in which it is perpendicular to the individual's gaze direction. The target is then preferably a light-emitting target, such as a light-emitting diode (LED).

In a variant, the measurement device may include automatic detection means for automatically detecting the relative position of the individual's head and the receiver members, in which the measurement axes of the emitter and receiver members are substantially perpendicular to the mean plane PM of the frame for a determined read position. The individual's head is then automatically situated at least in part in the reception cone of the receiver members for said read position.

By way of example, the automatic detection means then include means for scanning a range of possible angular positions of the receiver members relative to the display portion of the read medium, while ultrasound is being emitted, so that the measurement axes of those receiver members scan the individual's head 10. The range of scanning angular positions covers at least 15 degrees towards the front or towards the rear of the tablet relative to a reference mean angular position in which the angle GAMMA1 between the measurement axis of the receiver member and the display portion lies in the range 10 degrees to 80 degrees.

This scanning may be performed manually by the individual turning the knob of the device. It may also be performed automatically: pivoting of the measurement support is then motor-driven and controlled by electronic control means.

In a variant, the measurement support may be mounted on the tablet by means of a hinge, and scanning may be performed either manually by the individual causing the support to pivot by acting directly thereon, or automatically if pivoting of the support is motor-driven. No knob is then provided.

Automatic scanning presents the advantage of not involving the individual, who can continue to read the signs on the display portion 120. This limits the risk of the individual modifying the position of the tablet 110 while the angular position of the measurement support 130 is being adjusted.

This makes measurement more accurate.

Said computer and electronic means for processing ultrasound signals detected by the receiver members 151 then process the detected signals as a function of the angular position of the measurement support 130 and deduce the looked-for angular position therefrom.

In particular, the looked-for angular position corresponds to the position in which an intensity maximum is detected for the ultrasound signals.

Alternatively, the looked-for angular position corresponds to the position in which the intensity of the ultrasound signal is greater than a threshold.

By way of example, this threshold may correspond to a percentage of the intensity maximum of the ultrasound signal as obtained during a calibration step.

The duration of ultrasound emission up to detecting the maximum intensity of the signal is generally less than or equal to 40 seconds.

The electronic control means of the motor-driven scan means then cause the measurement support 130 to pivot to said angular position.

During the steps of pivoting the measurement support 130 towards its angular position in which the measurement axes of the emitter and receiver members are substantially perpendicular to the mean plane PM of the frame, the position of the individual's head 10 relative to the display portion 120 of the measurement device 100 does not change: the tablet 110 remains in the predefined reading position that is natural and comfortable for taking the measurement.

Once the measurement support 130 has been pivoted into the looked-for angular position, ultrasound emission is triggered and the ultrasound signal is detected.

By way of example, the duration of ultrasound emission and detection is equal to 10 seconds.

Figure 2:
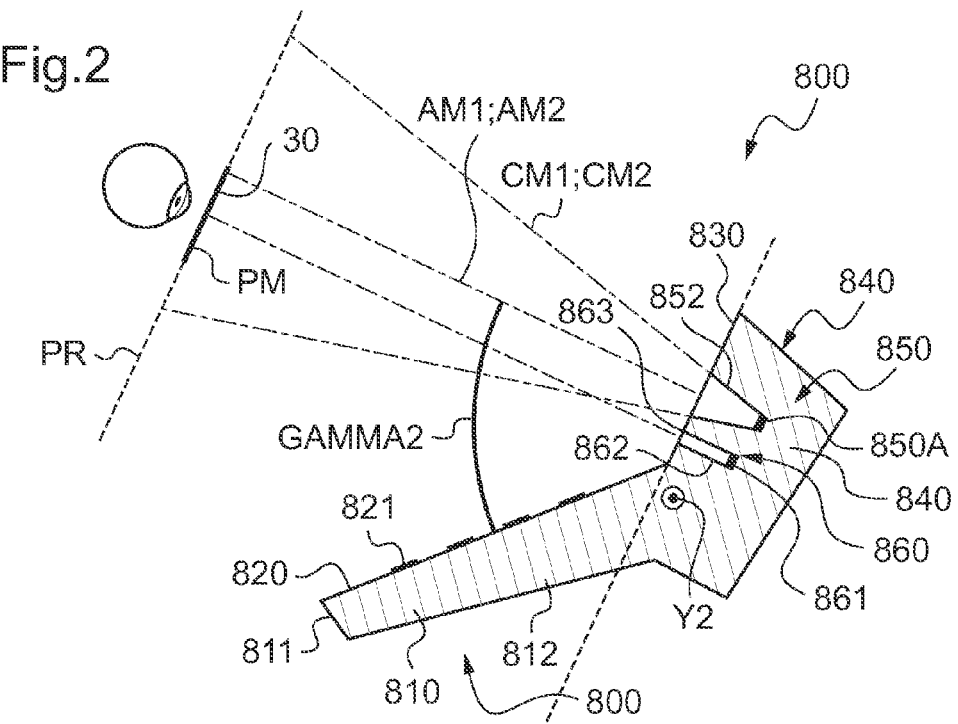
FIG. 2 is a diagrammatic profile view of an embodiment of the measurement device in the simplified embodiment of the invention.
Figure 3:
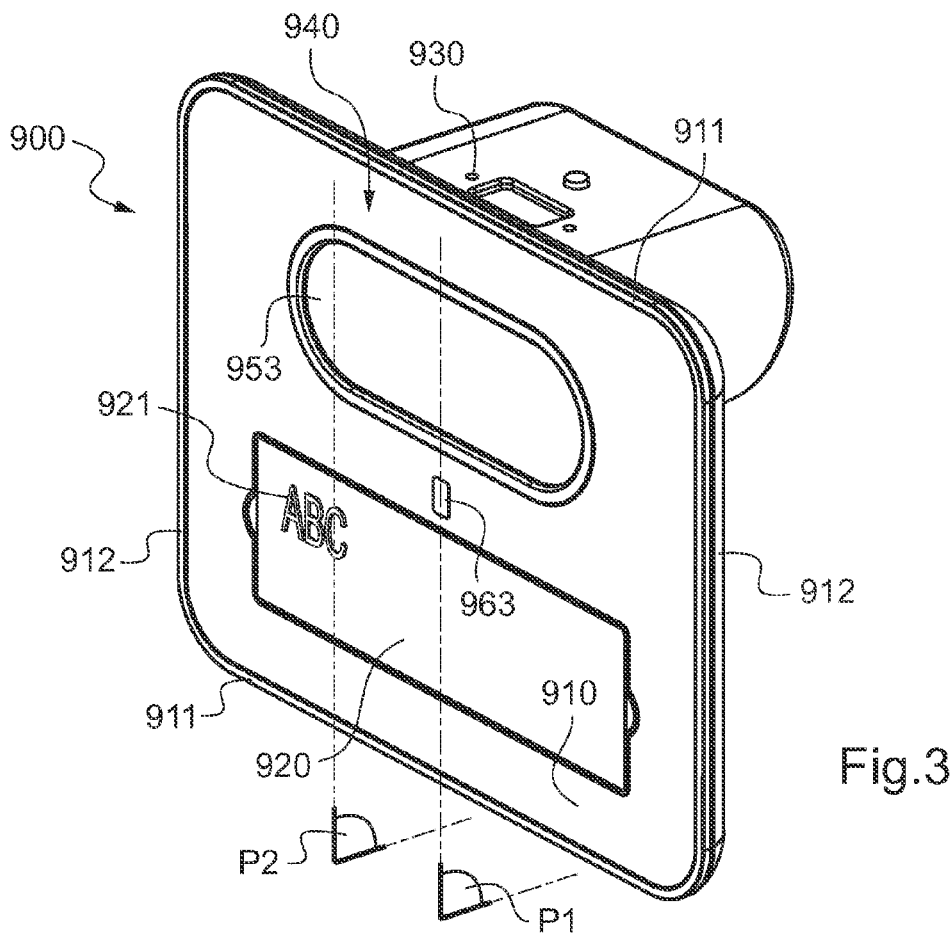
FIG. 3 is a diagrammatic perspective view of a preferred embodiment of the measurement device.

In the simplified embodiments of the invention shown in FIGS. 2 and 3, said measurement subassembly 840, 940 has two members that are both emitters and receivers 850 and 950.

As in the improved embodiment of the invention, these emitter-receiver members 850, 950 are aligned on a straight line parallel to the display lines of signs 821, 921 on the display portion 820, 920, and thus parallel to the transverse edges 811, 911 of the tablet 810, 910.

More precisely, the two emitter-receiver members 850, 950 are spaced apart by 7 centimeters. This spacing enables each emitter-receiver member 850, 950 to be placed facing a respective one of the ophthalmic lenses 31D, 31G of the individual's frame 30.

Remarkably, the emitter-receiver members 850, 950 are carried by the tablet 810, 910, and at least one of these emitter-receiver members 850, 950 possesses a measurement axis AM1, AM2, AM3, AM4 on which emission or reception by said measurement member is favored that is inclined relative to the plane of the display portion 820, 920 at an angle GAMMA2, GAMMA3 lying in the range 10 degrees to 80 degrees.

Under such circumstances, the emitter-receiver member 850, 950 is mounted to be stationary on the reading medium constituted by the tablet 810, 910 and that includes the display portion 820, 920.

More precisely, both emitter-receiver members 850, 950 are mounted stationary on the tablet 810, 910 and each of them possesses a respective measurement axis AM1, AM2, AM3, AM4 that is inclined relative to the plane of the display portion 820, 920 at a constant angle GAMMA2, GAMMA3 lying in the range 10 degrees to 80 degrees.

In this example the measurement subassembly 840, 940 includes a measurement support 830, 930 secured to the tablet 810, 910 and formed integrally with the tablet 810, 910, which support carries the emitter-receiver members 850, 950.

Each emitter-receiver member 850, 950 includes an emitter-receiver element placed at the end of a conical orifice 852, 952. The conical orifice 852 may be set back in the front face of the measurement support 830 or it may be defined by a conical shell 952 placed in a cavity 980 of larger size set back in the front face of the measurement support 930.

The measurement axis AM1, AM2, AM3, AM4 of each measurement member 850, 950 corresponds in this example to the axis of circular symmetry of the corresponding conical orifice 852, 952.

The measurement axes AM1, AM2, AM3, AM4 of both emitter-receiver members 850, 950 are parallel in this example.

In a variant, they may be inclined relative to each other so that they point in different directions. This configuration makes it possible to take account of strong curvature in the frame and the ophthalmic lenses worn by the individual.

The emitter-receiver members 850, 950 used in this example present respective measurement cones CM1, CM2, CM3, CM4 of mean aperture (FIGS. 2, 5) centered on the measurement axis AM1, AM2, AM3, AM4 constituting the privileged direction for ultrasound emission and reception of each of the emitter-receiver members 850, 950. These measurement cones CM1, CM2, CM3, CM4 present an angle at the apex lying in the range 15 degrees to 45 degrees, e.g. lying in the range 25 degrees to 35 degrees.

This mean aperture angle for the measurement cones of the emitter-receiver elements 850, 950 establishes a compromise between an aperture that is large enough to emit ultrasound towards the entire face of the individual, so as to make it easy to cover the individual's eyeglasses, and an aperture that is restricted so as to receive only ultrasound reflected on the individual's head and mainly on the individual's eyeglasses.

The angle GAMMA2, GAMMA3 between each measurement axis AM1, AM2, AM3, AM4 and the display portion 820, 920 lies for example in the range 60 degrees to 80 degrees, and is preferably equal to 70 degrees.

In the example shown in FIG. 2, each conical orifice 852 presents a diameter of 16 millimeters at the end of the conical orifice 852, a diameter of 32 millimeters where it opens out into the front face of the measurement support 830, and a depth of 50 millimeters.

In the preferred embodiment shown in FIGS. 3, 4, and 5, each conical orifice 952 (FIG. 5) comprises a conical shell housed in a larger-sized cavity 980 (FIG. 4). Each conical orifice 652 presents an angle at the apex of about 25 degrees.

In particularly advantageous manner, the front face of the measurement support 930 extends in the plane of the display portion 920. A plate 953 of material that is transparent to ultrasound closes the opening of each conical orifice 952. This configuration for the device 900 ensures that the front face facing towards the individual is plane. The device 900 then presents an appearance that is closer to that of a page or a screen on which the individual is used to reading. It is thus easier for the individual to take up a reading posture that is natural.

In addition, the device 900 is compact and easy to handle.

In this simplified embodiment of the invention, the individual initially places the measurement device 800, 900 at a distance and at an inclination that correspond to the individual's natural reading position so as to read the signs on the display portion 820, 920.

The ultrasound reflected along the measurement axis AM1, AM2, AM3, AM4 of each emitter-receiver member 850, 950 comes from a surface that is substantially perpendicular to the measurement axis AM1, AM2, AM3, AM4. It is thus preferable to tilt the measurement device 800, 900 in such a manner that this measurement axis AM1, AM2, AM3, AM4 is substantially perpendicular to the mean plane PM of the frame 30 of the individual's eyeglasses.

To do this, the individual pivots the measurement device 800, 900 as a whole from an initial orientation in which its inclination corresponds to the individual's natural reading position so as to place the emitter-receiver members 850, 950 in a measurement angular position in which they detect ultrasound with a maximum intensity or with an intensity greater than a threshold, which ultrasound is emitted by them and reflected by the eyeglass frame 30 placed on the individual's head 10.

In a variant, it may be envisaged that the emitter-receiver members receive ultrasound reflected by the individual's head or by some other accessory worn on the individual's head 10.

Performing this step ensures that the measurement axis AM1, AM2, AM3, AM4 of each emitter-receiver member 850, 950 is substantially perpendicular to the mean plane PM of the individual's eyeglass frame 30. Consequently, it automatically ensures that each emitter-receiver member 850 is in an angular position such that the individual's head is situated at least in part in the measurement cone CM1, CM2, thereof.

The individual preferably causes the reading medium to pivot about a horizontal axis Y2, Y3 of the measurement device 800, 900 parallel to the text on the display portion 120, 820, 920. Alternatively, the individual may also cause the reading medium to pivot about an axis perpendicular to said horizontal axis and parallel to the plane of the display portion.

In order to perform this step of placing the emitter-receiver members 850, 950 in the measurement angular position, the device includes visual detection means 860, 960 enabling said angular position to be detected visually.

These visual detection means 860, 960 comprise a target 861, 961 placed at the end of a cavity 862, 962 opening out into the front face of the measurement device via an opening 863, 963, such that the target is visible to the individual only in a predetermined angular range for the gaze direction that corresponds to the emitter-receiver members 850, 950 occupying an angular orientation relative to the individual's head 10 that is suitable for taking a measurement.

The target 861, 961 is preferably a light-emitting target. For example, it is an LED.

It is preferably located close to the two emitter-receiver members 950, as shown in FIG. 3, in a midplane P1 extending between the two emitter-receiver members. This target 961 is thus visible in the section view on plane P1 of FIG. 4.

It may also be located immediately below one of the emitter-receiver members 850, as shown in FIG. 2.

The individual then pivots the reading medium so as to see the target 961. In the example shown in FIG. 4, the target is visible only in a very narrow range of angles centered about an axis of symmetry AC of the cavity 962.

In a variant, as in the improved embodiment, the measurement device includes at least one target and at least one mark that are secured to the measurement device, the mark and the target being offset along the direction common to the measurement axes of the emitter-receiver members.

The individual then pivots the reading medium in such a manner as to visually center said target on said mark.

This adjustment ensures that the mean plane PM of the frame lies substantially perpendicular to the measurement axes AM1, AM2, AM3, AM3 of the emitter-receiver members 850, 950 in order to detect a signal of maximum intensity or at least greater than a threshold.

The threshold may be determined or it may be calibrated so as to be equal to a percentage of the maximum intensity, for example.

Then, in this configuration, the looked-for characteristic distance is measured as a function of the signal delivered by the emitter-receiver members representative of the ultrasound signal emitted by each emitter-receiver member 850, 950 and reflected by the individual's head 10 or by the accessory 30 worn on said individual's head 10.

This measurement is performed in a manner that is entirely similar to that described for the improved embodiment.

In a variant, the looked-for reading distance may be measured when the measurement device is initially placed at a distance and at an inclination that correspond to the individual's natural reading posture, without subsequently altering the inclination of the measurement device in order to orient it on its measurement angle of inclination.

Since the measurement axes of the measurement members form an angle lying in the range 60 degrees to 80 degrees relative to the plane display portion, and preferably equal to 70 degrees, it then remains possible to obtain a signal of intensity that is greater than the signal that would be detected if the measurement axes of the measurement members were perpendicular to the plane of the display portion, in conventional manner.

For the device to be used in this way, it is preferable for the emitter-receiver members to be selected so as to be not very directional, thus presenting measurement cones greater than 35 degrees, e.g. lying in the range 40 degrees to 50 degrees, in such a manner that the eyeglass frame worn by the individual comes at least in part within said measurement cone in the natural reading position.

Whatever the embodiment of the measurement device, the computer and electronic processing means of the measurement device 100, 800, 900 determines the looked-for characteristic reading distance, specifically the distance between the frame 30 (as in the example described) or the lenses (in an analogous variant that can easily be derived therefrom) of the eyeglass worn by the individual, and the measurement device 100, 800, 900. When the emitter-receiver member is located at the end of a conical orifice, the orifice acts as a waveguide, thereby contributing to amplifying the received signal.

The electronic processor unit is suitable for extracting from the ultrasound signal received by the receiver member, that portion of said signal that has been reflected by the lenses or the frame of the eyeglasses worn by the individual, while excluding the portion of said signal that is reflected by the individual's skin.

The intensity of the received signal depends on the nature of the material that has reflected the emitted ultrasound signal and on the difference between the angular position of the measurement axis of the emitter-receiver members and the measurement angular position in which said measurement axis is perpendicular to the mean plane of the frame.

The absolute amplitude of the received signal, i.e. its strength or intensity, makes it possible to determine whether the received signal comes from a reflection on the individual's skin or from a reflection on the eyeglass frame.

By way of example, for a characteristic reading distance of about 40 centimeters, the signal received after reflection on the frame is about four times stronger than the signal received after reflection on the skin.

It is thus easy to discriminate between a looked-for signal received after reflection on the eyeglass frame and a signal received after reflection on the skin, and this remains true even if the angular position of the measurement axes of the emitter-receiver members is not exactly the measurement angular position.

The electronic and computer processor means of the measurement device perform automatic gain control, i.e. they amplify the signal received by the receiver or emitter-receiver elements as a function of the amplitude of the received signal.

This amplitude depends in particular on the area of the eyeglasses carried by the individual. A small eyeglass frame will give rise to a received signal of amplitude that is smaller than an eyeglass frame of larger size.

Increasing amplification of the signal by the electronic and computer processor means of the measurement device enables this difference to be compensated.

In addition, in the event of a very intense peak in the signal, of amplitude greater than a first predefined threshold value, the electronic and computer processor means are programmed to peak-limit the signal prior to performing gain control.

The electronic and computer processor means of the measurement device detects the received signal of intensity greater than a second predetermined threshold value. This second threshold value preferably corresponds to an intensity value for the signal that ensures that the received signal comes from the emitted signal after reflection on the individual's eyeglass frame.

This second threshold value is determined from calibration measurements performed beforehand, or it corresponds to a predetermined standard value compared with the maximum signal expected for a frame of given size and for determined gain. By way of example, this standard value is taken to be equal to 20 percent of the maximum signal.

A plurality of threshold values lower than said second threshold value may be provided to take account of the decrease in the intensity of the received signal as a function of the difference between the angular position of the measurement axes of the emitter-receiver members and the measurement angular position.

Detection is then performed at these various threshold values in succession by the electronic and computer processor means of the measurement device in the event of a failure to detect a signal above a higher threshold value. The threshold values are applied in decreasing order until a signal is detected.

This thresholding technique serves to avoid failures of detection, which would make it necessary to perform a new measurement.

Naturally, if the received signal presents intensity that is lower than the lowest threshold value, then the measurement device issues an error message indicating that the measurement must be repeated.

Under ideal circumstances in which the receiver element receives only a signal reflected by the individual's eyeglasses, the signal received as a function of time presents a square waveform.

In reality, the ultrasound signal received after reflection on the wearer's head includes a component at shorter times, corresponding to the signal reflected by the individual's skin situated in front of the eyeglasses, followed by a component at intermediate times corresponding to the signal reflected by the individual's eyeglasses, and finally a component at longer times corresponding to the signal reflected by the individual's skin situated behind the eyeglasses relative to the measurement device.

The signal received by the receiver or emitter-receiver members then presents a shape that is approximately flat that is associated with the texture of the surface on which the ultrasound waves are reflected.

The means processing the received signal then perform a step of correcting the slope of the real received signal, which step corresponds to amplifying said slope in order to approach the ideal situation and determine more accurately the moment at which the signal reflected on the individual's eyeglasses is received.

By way of example, this moment is determined as the time corresponding to a threshold of the rising slope of the received signal, which threshold is a settable threshold (typically being situated between 50% and 20% of full height).

A first value of the characteristic reading distance between the individual's eyeglasses and the emitter-receiver members of the measurement device is then determined as a function of said time.

Preferably, once a first value of the looked-for distance has been determined, the received signal is also subjected to a calibration correction step corresponding to subtracting a reference signal corresponding to the signal as received when ultrasound waves are reflected by the skin.

This reference signal corresponds to the signal received by the receiver or emitter-receiver member after reflection on the skin of a mean reference individual's face when said reference individual is at a distance from the measurement device that is equal to the first value for the determined characteristic reading distance.

By way of example, this reference signal is determined by performing three calibration measurements at known characteristic reading distances, e.g. for characteristic reading distances of 30 centimeters, 40 centimeters, and 50 centimeters.

Linear interpolation between those signals makes it possible to deduce therefrom a reference signal for all characteristic reading distances lying in the range 30 centimeters to 50 centimeters.

The electronic and computer processor means acting on the signal subtract from the received signal the reference signal that corresponds to the first value determined for the characteristic reading distance.

The above steps are then repeated on said corrected signal so as to determine a second value for the characteristic reading distance that is more accurate than the first value.

The accuracy of the measurement as performed in this way is about 1 centimeters to 2 centimeters.

The total duration of measurement is preferably less than or equal to 1 minute and 15 seconds. This measurement is thus performed very quickly.

More particularly in this example, a first looked-for characteristic reading distance is determined as the average of the ultrasound signals detected by the two receiver members 151 or emitter-receiver members 850, 950 of the measurement subassembly 140, 840, 940 and processed by the electronic and computer processor means, as explained above.

These two receiver members 151 or emitter-receiver members 850, 950 of the measurement subassembly 140, 840, 940 are each located facing a respective one of the ophthalmic lenses of the individual's eyeglass frame 30, and each of them gives a measurement of the characteristic distance between a respective one of the ophthalmic lenses of said frame 30 and the corresponding receiver member 151 or emitter-receiver member 850, 950.

The first mean characteristic distance thus corresponds to a mean of the distances between each of the lenses and the measurement device.

Taking this mean serves to limit the influence on the measurement of a small amount of rotation of the head about a vertical axis: this serves to limit the error introduced by the fact that the sagittal plane PSAG of the wearer's head does not coincide exactly with the plane of symmetry PS of the measurement device.

The measurements are preferably repeated and averaged: the looked-for characteristic reading distance is determined from the average of at least five first characteristic distances as determined in this way.

In a variant, the electronic and computer processor means determine two characteristic distances from ultrasound signals received by each of the two receiver members corresponding respectively to measuring the distance between each of the ophthalmic lenses and the tablet. The electronic and computer processor means then average these two distances in order to determine the looked-for characteristic reading distance. A plurality of these values may then be averaged in order to obtain a more accurate mean characteristic reading distance.

The measurement device 100, 800, 900 also optionally includes means for transmitting, wirelessly or otherwise, the distance measurement performed to one or more other devices used by the optician.

In particular, the measurement device 100, 800, 900 may be a measurement unit forming part of some greater measurement kit.

The measurement device 100, 800, 900 may also include means for displaying the characteristic reading distance as determined. The distance may then be read directly from the measurement device by the individual or by the optician.

The measurement device 100, 800, 900 preferably includes independent power supply means, e.g. optionally-rechargeable batteries. Such batteries 970 are visible in the preferred embodiment of the invention as shown in FIG. 3.

The present invention is not limited in any way to the embodiments described and shown, and the person skilled in the art is capable of applying any variant thereto in accordance with its spirit.

By way of example, the measurement device may include additional on-board measuring instruments, e.g. an inclinometer suitable for measuring the angle of inclination between the plane of the display portion of the measurement device and a horizontal plane. This inclination may be taken into account in order to improve the accuracy of the distance measurements taken.

The various improved embodiment variants described may be combined. In particular, each embodiment variant envisaged in the description for an emitter member presenting a broad emission cone and two receiver members each presenting a narrow reception cone may be applied to an emitter member having a narrow emission cone associated with receiver members each presenting a broad reception cone.

It is possible to envisage that the measurement subassembly is capable of pivoting in more than one direction: the measurement support would then be mounted on the reading medium via a ball joint.

It is possible to envisage that the measurement member, whether a receiver or an emitter, is movably mounted directly on the tablet, without any intermediate measurement support. It is then possible, for example, for it to be motor-driven and pointable relative to the tablet.

It is also possible to envisage that the display portion of the reading medium may be constituted by a removable display device. The removable display device may for example be a mobile telephone or a multimedia tablet that may be provided by the optician or that may belong to the individual. The reading medium then includes a docking station for the removable display device.

Other means for visually detecting the measurement angle of inclination of the measurement device may be envisaged. In particular, it is possible for example to provide for the visual detection means to be associated with signs displayed by the display portion of the measurement device. The signs are then visible to the individual only at an angle of incidence in which the measurement device is oriented with the measurement angle of inclination.

In the preferred embodiment, the display portion may include the plate of ultrasound-transparent material that closes the opening of each conical orifice, in such a manner that the signs read by the individual lie in front of the opening of the conical orifices of the emitter-receiver members. The measurement of the characteristic reading distance of the individual is then more accurate since the individual is looking at the emitter-receiver members.

Furthermore, using signs that are visible only at certain angles of incidence and that therefore form the visual detection means, the measurement device as obtained in this way is particularly compact and enables a very accurate measurement to be taken.

The different simplified embodiment variants described above may be combined.

The invention claimed is:

1. A measurement device (800, 900) for measuring a characteristic reading distance of an individual in a natural posture for near vision, wearing eyeglasses comprising a lens and a frame, the device comprising:
   a portable or freely movable reading medium (810, 910) presenting a plane display portion (820, 920) suitable for displaying signs; and
   a measurement subassembly (840, 940) including at least one ultrasound emitter member (850, 950) and at least one ultrasound receiver member (850, 950),
   wherein the emitter and receiver members (850, 950) are carried by the reading medium (810, 910), and wherein at least one of said members, referred to as the first measurement member (850, 950) possesses a measurement axis (AM1, AM2, AM3, AM4) along which emission or reception by the first measurement member is optimally provided and that is inclined relative to the plane of the display portion (820, 920) by a constant angle (GAMMA2, GAMMA3) lying in the range from 10 degrees to 80 degrees, and wherein, at least a portion of the signal received by the receiver member being reflected by the lenses or frame of the eyeglasses worn by the individual, said device includes an electronic processor unit that is suitable for extracting from the ultrasound signal received by the receiver member that portion of said signal that is reflected by the lenses or the frame of eyeglasses worn by the individual, to the exclusion of the portion of said signal that is reflected by the individual's skin.

2. The measurement device (800, 900) according to claim 1, wherein the first measurement member (850, 950) is mounted stationary on the reading medium (810, 910).

3. A measurement device for measuring a characteristic reading distance of an individual in a natural posture for near vision, wearing eyeglasses comprising a lens and a frame, the device comprising:
   a portable or freely movable reading medium (110) presenting a plane display portion (120) suitable for displaying signs; and
   a measurement subassembly (140) including at least one ultrasound emitter member (150) and at least one ultrasound receiver member (151),
   wherein the emitter (150) and receiver members (151) are carried by the reading medium (110), and wherein at least one of said members, referred to as the first measurement member (150, 151) possesses a measurement axis (AME, AMR) along which emission or reception by the first measurement member (151) is optimally provided and that is inclinable relative to the plane of the display portion (120) at least over an angular range extending from 10 degrees to 80 degrees, and
   wherein at least a portion of the signal received by the receiver member being reflected by the lenses or frame of the eyeglasses worn by the individual, said device includes an electronic processor unit that is suitable for extracting from the ultrasound signal received by the receiver member that portion of said signal that is reflected by the lenses or the frame of eyeglasses worn by the individual, to the exclusion of the portion of said signal that is reflected by the individual's skin.

4. The measurement device (100) according to claim 3, wherein the first measurement member (150, 151) is movably mounted on the reading medium (110) to be capable at least of pivoting relative to the plane of said display portion (120) of the reading medium.

5. The measurement device (100) according to claim 3, wherein at least one emitter member (150) and at least one receiver member (151) are mounted to pivot together on the reading medium (110).

6. The measurement device (100) according to claim 3, wherein said first measurement member (150, 151) presents a measurement cone (CE, CR) centered on its measurement axis (AME, AMR), the angle at the apex of the cone being less than 45 degrees.

7. The measurement device (100) according to claim 6, including visual detection means (160) enabling the individual to detect visually a relative position of said first measurement member (150, 151) and the head (10) of the individual in which the individual's head (10) is situated at least in part in the measurement cone (CE, CR) of said first measurement member (150, 151), in a determined relative position of the head (10) and the reading medium (110).

8. The measurement device according to claim 6, including automatic detection means for automatically detecting a relative position of said first measurement member and the head of the individual in which the individual's head is situated at least in part in the measurement cone of said first measurement member, in a determined relative position of the head and the reading medium.

9. The measurement device according to claim 8, wherein said automatic detection means include means for scanning a range of angular positions of said first measurement member relative to the display portion of the reading medium, so that the measurement axis of the first measurement member scans the individual's head.

10. A method of measuring a characteristic reading distance of an individual in a natural posture in near vision, wearing eyeglasses comprising a lens and a frame, the method comprising the following steps:
    a1) providing the individual with a measurement device (800, 900) comprising:
        a portable or freely movable reading medium (810, 910) presenting a plane display portion (820, 920) suitable for displaying signs; and
        a measurement subassembly (840) including at least one ultrasound emitter member (850, 950) and at least one ultrasound receiver member (850, 950) carried by the reading medium, at least one of said members, referred to as a first measurement member (850, 950) mounted in stationary manner on the reading medium (810, 910) and possessing a measurement axis (AM1, AM2, AM3, AM4) along which emission or reception by the first measurement member (850, 950) is optimally provided and that is inclined relative to the plane of the display portion (820, 920) by a constant angle (GAMMA2, GAMMA3) lying in the range from 10 degrees to 80 degrees;
    b1) the individual positioning the display portion (820, 920) of the reading medium (810, 910) in an appropriate reading position enabling the individual to read the signs on the display portion; and
    d1) in the configuration defined in step b1), determining the looked-for characteristic reading distance as a function of the signal received by the receiver member (850, 950) and representative of the ultrasound signal emitted by the emitter member (850, 950) and reflected by the individual's head (10) or by an accessory (30) worn by the head,
    wherein, at least a portion of the signal received by the receiver member being reflected by the lenses or frame of the eyeglasses worn by the individual, said method includes a step of extracting from the ultrasound signal received by the receiver member that portion of said signal that is reflected by the lenses or the frame of eyeglasses worn by the individual, to the exclusion of the portion of said signal that is reflected by the individual's skin.

11. The method according to claim 10, further including the following step c1):
    in a reading position set in step b1), causing the reading medium (810, 910) as a whole to pivot so as to place said first measurement member (850, 950) in an angular position in which the receiver member (850, 950) picks up, with maximum intensity or intensity greater than a threshold, the ultrasound emitted by the emitter member (850, 950) and reflected by the head (10) of the individual or by an accessory (30) worn on the head,
    wherein in step d1), the looked-for characteristic reading distance is determined in the configuration defined in steps b1) and c1).

12. The measurement method according to claim 10, wherein, in step c1), for said first measurement member (850, 950) presenting a measurement cone (CM1, CM2) having an angle at the apex of less than 45 degrees, the reading medium (810, 910) is caused to pivot to place said first measurement member (850, 950) in an angular position such that the individual's head (10) is situated at least in part in the measurement cone (CM1, CM2, CM3, CM4) of the first measurement member (850, 950).

13. The measurement method according to claim 11, wherein, in step c1), for the device including at least one target and at least one mark secured to said first measurement member, the mark and the target being offset from each other along the direction of the measurement axis of the measurement member, the individual causes the reading medium to pivot in such a manner as to center said target on said mark visually.

14. The measurement method according to claim 11, wherein for the device (800, 900) including at least one target (861, 961) secured to said first measurement member (850, 950) and located at the end of a cavity (862, 962) in such a manner that the target is visible to the individual only in a predetermined range of orientation angles of the measurement member (850, 950) relative to the individual's head (10), in step c1), the individual causes the reading medium (810, 910) to pivot in such a manner as to be able to see the target (861, 961).

15. The measurement method according to claim 11, wherein, in step c1), the reading medium (810, 910) is caused to pivot about a horizontal axis (Y2) situated in the mean plane of the reading medium (810, 910).

16. A method of measuring a characteristic reading distance of an individual in a natural posture and in near vision, wearing eyeglasses comprising a lens and a frame, the method comprising the following steps:
    a2) providing the individual with a measurement device (100) comprising:
        a portable or freely movable reading medium (110) presenting a plane display portion (120) suitable for displaying signs; and a measurement subassembly (140) including at least one ultrasound emitter member (150) and at least one ultrasound receiver member (151) carried by the reading medium, at least one of these members (150, 151), referred to as the first measurement member (150, 151) being mounted on the reading medium (110) to be capable at least of pivoting relative to said display portion (120) of the reading medium (110) and possessing a measurement axis (AME, AMR) along which the emission or the reception by the first measurement member (150, 151), is optimally provided, b2) the individual positioning the display portion (120) of the reading medium (110) in a suitable reading position enabling the individual to read the signs of the display portion (120);

c2) in this reading position set in step b2), causing said first measurement member (150, 151) to pivot relative to the display portion (120) to place said first measurement member (150, 151) in an angular position in which the receiver member (151) picks up, with maximum intensity or intensity greater than a threshold, the ultrasound emitted by the emitter member (150) and reflected by the individual's head (10) or by an accessory (30) worn by the head; and d2) in the configuration defined in steps b2) and c2), determining the looked-for characteristic reading distance (D) as a function of the signal received by the receiver member (151) and representative of the ultrasound signal emitted by the emitter member (150) and reflected by the individual's head (10) or by an accessory (30) worn by the head, wherein at least a portion of the signal received by the receiver member being reflected by the lenses or frame of the eyeglasses worn by the individual, said method includes a step of extracting from the ultrasound signal received by the receiver member that portion of said signal that is reflected by the lenses or the frame of eyeglasses worn by the individual, to the exclusion of the portion of said signal that is reflected by the individual's skin.

17. The measurement method according to claim 16, wherein, in step c2), for said first measurement member (150, 151) presenting a measurement cone (CE, CR) having an angle at the apex of less than 45 degrees, said first measurement member (150, 151) is caused to pivot relative to the display portion (120) to place it in an angular position in which the individual's head (10) is situated at least in part in the measurement cone (CE, CR) of the first measurement member (150, 151).

18. The measurement method according to claim 16, wherein in step c2), for the device (100) including at least one target (161) and at least one mark (150) secured to said first measurement member (150, 151), the mark (150) and the target (161) being offset along the direction of the measurement axis (AME, AMR) of the first measurement member, the individual causes the first measurement member (150, 151) to pivot in such a manner as to center said target (161) on said mark (150) visually.

19. The measurement method according to claim 16, wherein, for the device including at least one target secured to said first measurement member and located at the end of a cavity in such a manner that the target is visible to the individual only over a predetermined range of orientation angles of the measurement member relative to the individual's head, in step c2) the individual causes the first measurement member to pivot in such a manner as to be able to see the target.

20. The measurement method according to claim 16, wherein, in step c2), the following steps are performed:

causing the ultrasound emitter member (150) to emit ultrasound;

manually or automatically scanning the various possible angular positions of the first measurement member (150, 151) during ultrasound emission;

detecting an ultrasound signal as emitted and reflected by the individual's head (10) or by an accessory (30) worn by the head during said scanning; and as a function of the detected signal, determining the looked-for angular position of the first measurement member (150, 151) in which the receiver member (151) picks up the ultrasound emitted by the emitter member (150) and reflected by the individual's head (10) or by an accessory (30) worn by the head.

21. The measurement method according to claim 20, wherein, in step c2), the first measurement member (150, 151) is caused to pivot relative to the display portion (120) of the reading medium (110) about a horizontal axis (X) situated in the mean plane of the reading medium (110).

22. A measurement device for measuring a characteristic reading distance of an individual in a natural posture for near vision, the device comprising:

a portable or freely movable reading medium (110) presenting a plane display portion (120) suitable for displaying signs; and a measurement subassembly (140) including at least one ultrasound emitter member (150) and at least one ultrasound receiver member (151), wherein, the emitter (150) and receiver members (151) are carried by the reading medium (110), and wherein at least one of said members, referred to as the first measurement member (150, 151) possesses a measurement axis (AME, AMR) along which emission or reception by the first measurement member (151) is optimally provided and that is inclinable relative to the plane of the display portion (120) at least over an angular range extending from 10 degrees to 80 degrees, and the measurement device including automatic detection means for automatically detecting a relative position of said first measurement member and the head of the individual in which the individual's head is situated at least in part in the measurement cone of said first measurement member, in a determined relative position of the head and the reading medium.

23. The measurement device (100) according to claim 22, wherein the first measurement member (150, 151) is movably mounted on the reading medium (110) to be capable at least of pivoting relative to the plane of said display portion (120) of the reading medium.

24. The measurement device (100) according to claim 22, wherein at least one emitter member (150) and at least one receiver member (151) are mounted to pivot together on the reading medium (110).

25. The measurement device (100) according to claim 22, wherein said first measurement member (150, 151) presents a measurement cone (CE, CR) centered on its measurement axis (AME, AMR), the angle at the apex of the cone being less than 45 degrees.

26. The measurement device according to claim 22, wherein said automatic detection means include means for scanning a range of angular positions of said first measurement member relative to the display portion of the reading medium, so that the measurement axis of the first measurement member scans the individual's head.

27. A method of measuring a characteristic reading distance of an individual in a natural posture and in near vision, the method comprising the following steps:

- a3) providing the individual with a measurement device (100) comprising:
  - a portable or freely movable reading medium (110) presenting a plane display portion (120) suitable for displaying signs; and
  - a measurement subassembly (140) including at least one ultrasound emitter member (150) and at least one ultrasound receiver member (151) carried by the reading medium, at least one of these members (150, 151), referred to as the first measurement member (150, 151) being mounted on the reading medium (110) to be capable at least of pivoting relative to said display portion (120) of the reading medium (110) and possessing a measurement axis (AME, AMR) along which the emission or the reception by the first measurement member (150, 151), is optimally provided,
- b3) the individual positioning the display portion (120) of the reading medium (110) in a suitable reading position enabling the individual to read the signs of the display portion (120);
- c3) in this reading position set in step b3), causing said first measurement member (150, 151) to pivot relative to the display portion (120) to place said first measurement member (150, 151) in an angular position in which the receiver member (151) picks up, with maximum intensity or intensity greater than a threshold, the ultrasound emitted by the emitter member (150) and reflected by the individual's head (10) or by an accessory (30) worn by the head; and
- d3) in the configuration defined in steps b3) and c3), determining the looked-for characteristic reading distance (D) as a function of the signal received by the receiver member (151) and representative of the ultrasound signal emitted by the emitter member (150) and reflected by the individual's head (10) or by an accessory (30) worn by the head, wherein, the method includes a step of automatically detecting a relative position of said first measurement member and the head of the individual in which the individual's head is situated at least in part in the measurement cone of said first measurement member, in a determined relative position of the head and the reading medium.

* * * * *

UNITED STATES PATENT AND TRADEMARK OFFICE
CERTIFICATE OF CORRECTION

| | | |
|---|---|---|
| PATENT NO. | : 8,794,762 B2 | Page 1 of 1 |
| APPLICATION NO. | : 13/113114 | |
| DATED | : August 5, 2014 | |
| INVENTOR(S) | : Ahmed Haddadi | |

It is certified that error appears in the above-identified patent and that said Letters Patent is hereby corrected as shown below:

In The Specification

In column 21, lines 16-19, please amend the paragraph to read as follows:

-- The measurement device 100, 800, 900 preferably includes independent power supply means, e.g. optionally-rechargeable batteries. Such batteries 970 are visible in the preferred embodiment of the invention as shown in Figure 4. --

Signed and Sealed this
Fourteenth Day of April, 2015

Michelle K. Lee
*Director of the United States Patent and Trademark Office*